(12) United States Patent
Hanssen

(10) Patent No.: US 9,718,664 B2
(45) Date of Patent: Aug. 1, 2017

(54) CLOSING VALVE AND CONTAINER COMPRISING THE SAME

(75) Inventor: Hubert Joseph Frans Hanssen, Amsterdam (NL)

(73) Assignee: EUROKEG B.V., Den Helder (NL)

( * ) Notice: Subject to any disclaimer, the term of this patent is extended or adjusted under 35 U.S.C. 154(b) by 455 days.

(21) Appl. No.: 12/602,136

(22) PCT Filed: May 29, 2008

(86) PCT No.: PCT/EP2008/056628
§ 371 (c)(1),
(2), (4) Date: Mar. 30, 2010

(87) PCT Pub. No.: WO2008/145702
PCT Pub. Date: Dec. 4, 2008

(65) Prior Publication Data
US 2010/0176162 A1    Jul. 15, 2010

(30) Foreign Application Priority Data
May 30, 2007    (EP) .................................... 07109178

(51) Int. Cl.
*B67D 1/08*    (2006.01)
*A61M 39/26*    (2006.01)

(52) U.S. Cl.
CPC ......... *B67D 1/0871* (2013.01); *B67D 1/0832* (2013.01); *B67D 1/0878* (2013.01);
(Continued)

(58) Field of Classification Search
USPC ......... 251/149.6; 137/320, 322, 543.15, 317, 137/321, 323; 267/158, 160, 163
See application file for complete search history.

(56) References Cited

U.S. PATENT DOCUMENTS 1,345,965 A    7/1920    Shute
3,203,026 A *  8/1965    Schwartzman ............... 401/206
(Continued)

FOREIGN PATENT DOCUMENTS

EP    1652813 A1    5/2006
FR    2495112 A1    6/1982
(Continued)

OTHER PUBLICATIONS

Official Search Report of the European Patent Office in counterpart foreign application No. PCT/EP2008/056628 filed May 29, 2008.
(Continued)

*Primary Examiner* — Kevin Murphy
*Assistant Examiner* — Jonathan Waddy
(74) *Attorney, Agent, or Firm* — Steven M. Koehler; Westman, Champlin & Koehler, P.A.

(57) ABSTRACT

A closing valve for a container for a fluid includes an outer jacket connected or connectable to an opening in the container or forming part of the container. An inner jacket is accommodated inside the outer jacket and has an opening through which the fluid can be fed to or withdrawn from the container. A closing element is positioned inside the inner jacket or between the inner jacket and the outer jacket and movable between at least a first position closing the opening and a second position clearing the opening, wherein at least the closing element is made from a polymer material. The closing element comprises a sealing member and a spring, which urges the closing element into the first position.

17 Claims, 3 Drawing Sheets

(52) U.S. Cl.
CPC ........... B67D 1/0888 (2013.01); *A61M 39/26* (2013.01); *Y10T 137/613* (2015.04)

(56) References Cited

U.S. PATENT DOCUMENTS

| | | | | |
|---|---|---|---|---|
| 4,286,636 A | * | 9/1981 | Credle | 141/114 |
| 4,421,296 A | * | 12/1983 | Stephens | 251/149.7 |
| 4,601,413 A | * | 7/1986 | Krawagna | 222/498 |
| 4,635,683 A | * | 1/1987 | Nielsen | 137/625.65 |
| 4,665,940 A | * | 5/1987 | Jacobson | 137/212 |
| 4,667,921 A | * | 5/1987 | de Goncourt | F16F 1/18 248/618 |
| 4,756,347 A | * | 7/1988 | Hagan | B65D 83/425 137/212 |
| 5,203,477 A | * | 4/1993 | Lo | 222/153.01 |
| 5,255,713 A | * | 10/1993 | Scholle et al. | 137/614.04 |
| 5,511,692 A | * | 4/1996 | Willingham | 222/1 |
| 5,624,193 A | * | 4/1997 | Vogelsberger | F16C 25/083 267/163 |
| 6,357,723 B2 | * | 3/2002 | Kennedy | F04B 43/0736 137/903 |
| 7,121,493 B2 | * | 10/2006 | Hiraguchi | G11B 23/037 242/345.2 |
| 7,455,082 B2 | * | 11/2008 | Monzel | 141/18 |
| 2005/0178462 A1 | * | 8/2005 | Py | 141/2 |
| 2006/0000459 A1 | * | 1/2006 | Freeman et al. | 123/574 |
| 2007/0290010 A1 | * | 12/2007 | Nini | 222/511 |

FOREIGN PATENT DOCUMENTS

| | | |
|---|---|---|
| WO | WO 94/06703 | 3/1994 |
| WO | WO 00/07902 | 2/2000 |

OTHER PUBLICATIONS

Written Report of the European Patent Office in counterpart foreign application No. PCT/ EP2008/056628 filed May 29, 2008.

* cited by examiner

CLOSING VALVE AND CONTAINER COMPRISING THE SAME

CROSS-REFERENCE TO RELATED APPLICATION

The present application is a national stage filing of International patent application Ser. No. PCT/EP2008/056628, filed May 29, 2008, and published as WO 2008/145702 in English.

BACKGROUND

The discussion below is merely provided for general background information and is not intended to be used as an aid in determining the scope of the claimed subject matter.

Aspects of the invention relate to a closing valve for a container, and a container, for a fluid, such as a liquid, e.g. beer or soft drinks under pressure.

WO 00/07902 relates to a closing valve for a container comprising a closing jacket connected therewith, which closing jacket is provided on the inside with a narrowed and a widened portion, and a valve part movable in this closing jacket. This valve part has a closing element and a clamping element which is provided on at least the outside with a thickening which, when the passage through the closing jacket is sealed by the valve part, cooperates with the widened portion in the closing jacket. Furthermore, a head part movable in the closing jacket back and forth is provided, by means of which the valve part can be moved with respect to the closing jacket such that the passage therethrough can be released and/or closed, while when releasing the passage through the closing jacket, the thickening on the outside of the clamping element is brought into the narrowed portion of the closing jacket, as a result of which the clamping element reaches a position in which it is engaged by the head part.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background.

An aspect of the present invention provides relatively low cost closing valves which are suitable for use with standardized or at least commonly used dispense heads and which provide, e.g., European or American Sankey type keg fitting, German slider keg fitting or Grundy type keg fitting, also referred to as S, D, A or G type interface, respectively.

To this end, the polymer closing element comprises a sealing member and a spring, which spring urges the closing element into a first, closing position.

resilience provided by the closing element renders the operating mechanism of the closing valve compatible with most dispense heads.

In case of e.g. a Sankey type keg fitting, the closing element is positioned inside the inner jacket and, in case of e.g. a German slider or Grundy type keg fitting, the closing element is positioned between the inner jacket and the outer jacket, as will be explained in more detail below.

In one embodiment, the spring is an integral part of the closing element and comprises one or more, e.g. two or more resilient projections, e.g. leaf springs.

To provide at least substantially constant strain along length of the projection(s), the thickness of the projection(s) gradually decreases in a direction away from the sealing member.

In a further embodiment, the maximum strain level in the spring is less than 1%, e.g. less than 0.5%, when the closing element is in the first position, and/or less than the proportional limit, e.g. less than 3%, when the closing element is in the second position.

An aspect of the invention further relates to a container for fluids, in particular liquids, such as beer or water, comprising an outer casing, e.g. a spheroid outer casing made of a rigid material, a gas and/or liquid tight inner casing of a flexible material located inside the outer casing, and a closing valve as described above.

BRIEF DESCRIPTION OF THE DRAWINGS

Aspects of the invention will now be explained in more detail with reference to the drawings, which show various embodiments of the present invention.

Figure 1:
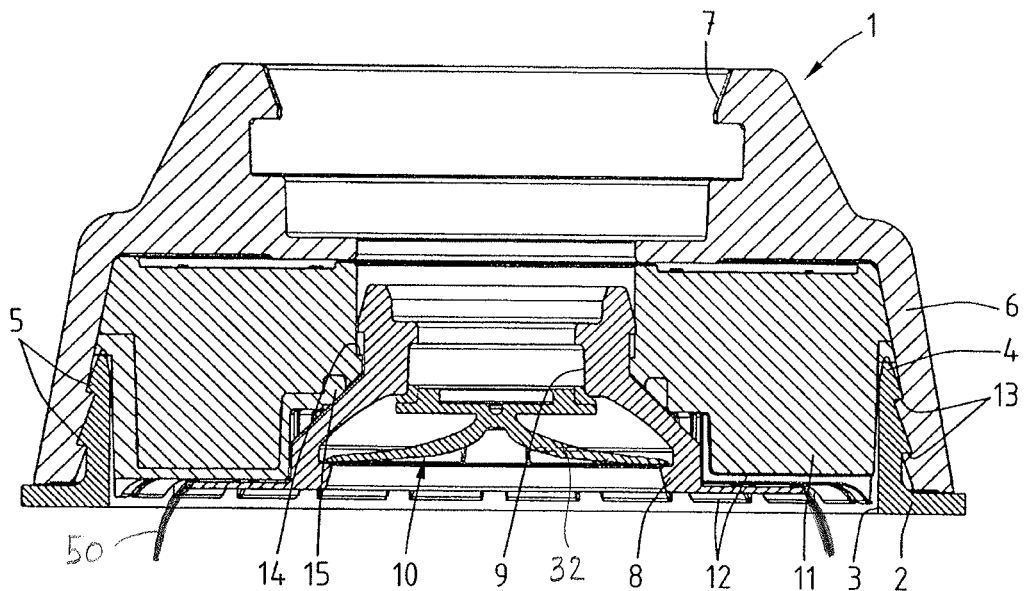
FIGS. 1 and 2 show cross-sections of a first embodiment of a closing valve according to an aspect of the present invention, in closed and opened conditions, respectively.

The drawings are not necessarily to scale and details, which are not necessary for understanding the present invention, may have been omitted. Further, elements that are at least substantially identical or that perform an at least substantially identical function are denoted by the same numeral. Furthermore, terms as "upper", "lower", and the like relate to the orientation of elements as shown in the drawings.

DETAILED DESCRIPTION OF THE ILLUSTRATIVE EMBODIMENTS

Figure 2:
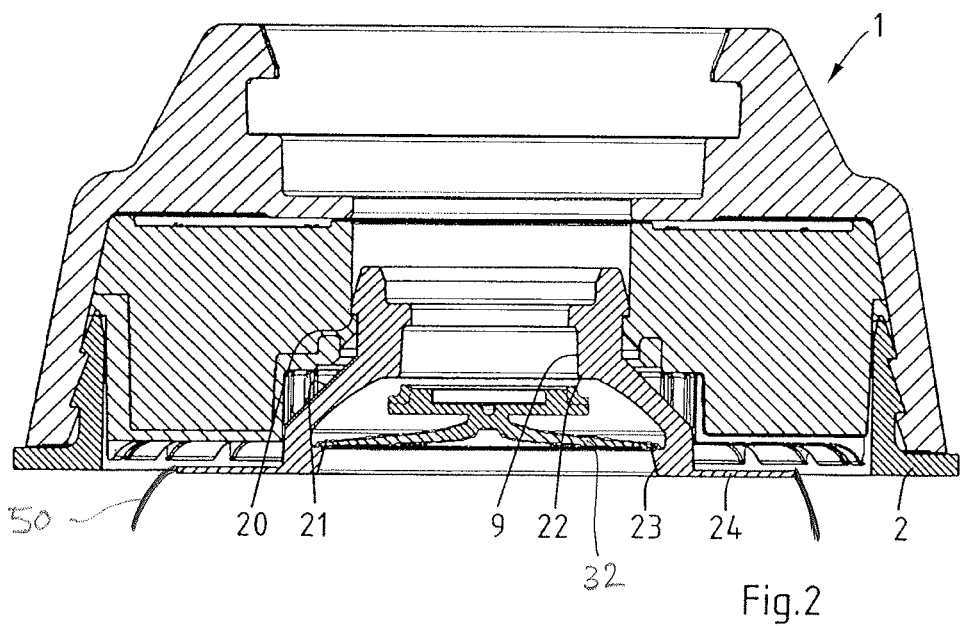

FIGS. 1 and 2 show cross-sections of a first embodiment of a closing valve 1 according to an aspect of the present invention, in closed and opened conditions, respectively, mounted on a container for a fluid, such as a liquid, e.g. beer or soft drinks under pressure. The container may, e.g. comprise a pressure resistant outer casing 2 having a central opening 3, defined by a circular rim 4, and a gas tight inner casing 50 of a flexible material located inside the outer casing 2. In this example, the rim 4 is provided with one or more, e.g. two, annular and upwardly tapering ledges 5 for establishing a snap-fit connection with the closing valve 1, as will be explained in more detail below.

The closing valve 1 comprises an outer jacket 6, having a so-called European Sankey keg fitting 7 or S type interface and an inner jacket 8, slidably accommodated inside the outer jacket 4 and having an opening 9 through which the fluid can be fed to or withdrawn from the container 2. The closing valve 1 further comprises a closing element 10 positioned inside the inner jacket 8 and slidable between at least a first position closing the opening 9 (FIG. 1) and a second position clearing the opening 9 (FIG. 2).

Figure 4:
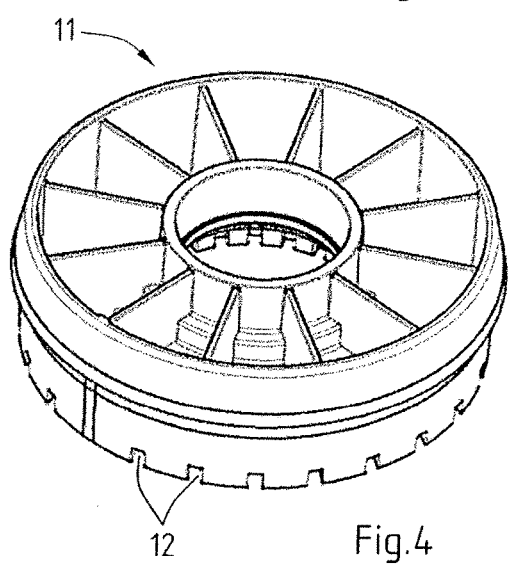
FIG. 4 is a perspective view of an inner ring for use in the closing valve according to FIGS. 1 and 2.

The outer jacket 6 comprises, in its bottom surface and preferably on a separate element, e.g. an inner ring 11, to facilitate manufacture, a plurality of radially extending channels or, in this case, venting grooves 12 (see also FIG. 4). The outer jacket 6, including the inner ring 11, is made of a polymer material, e.g. a glass or carbon fiber reinforced polyamide (PA). The inner wall of the outer jacket 6 comprises one or more, e.g. two, annular and downwardly tapering counter-ledges 13. Thus, the closing valve 1 can be snap-fitted substantially irreversibly to the container. Further, the outer jacket 6 or, in this example, the inner ring 11 comprises an annular stop 14 facing upwards and an annular gasket 15, both cooperating with the inner jacket 8.

The inner jacket 8 comprises, near its upper edge, an annular stop 20 and a conical sealing surface 21. The inner jacket 8 is made of a polymer material, e.g. a polyolefin, such as polyethylene (PE). The inner jacket 8 further comprises a seat 22 and, near its lower rim, an annular ledge 23 facing upwards. At its lower edge, the inner jacket 8 comprises a flange 24 to which an inner casing 50 for containing the fluid has been attached, e.g. by welding or gluing.

Figure 3A:
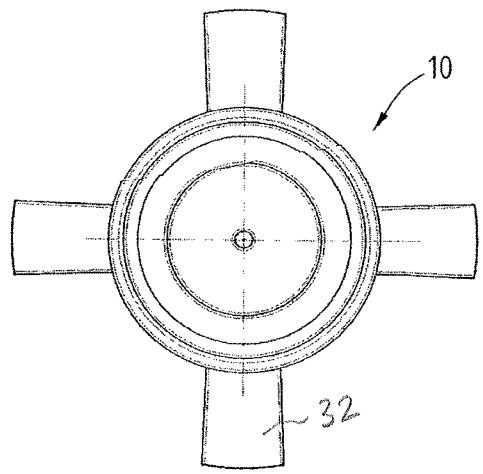
FIGS. 3A to 3E are a top, side, and bottom view, a cross-section, and a perspective view of a closing element for use in the closing valve according to FIGS. 1 and 2.
Figure 3D:
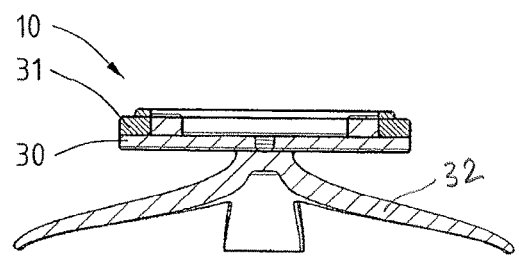
Figure 3B:
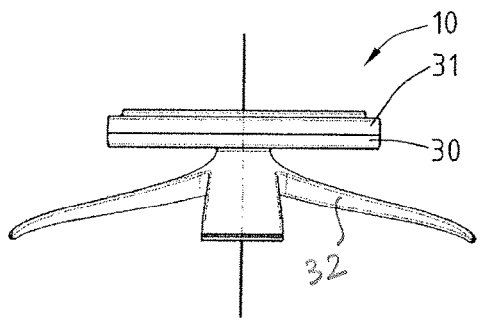
Figure 3E:
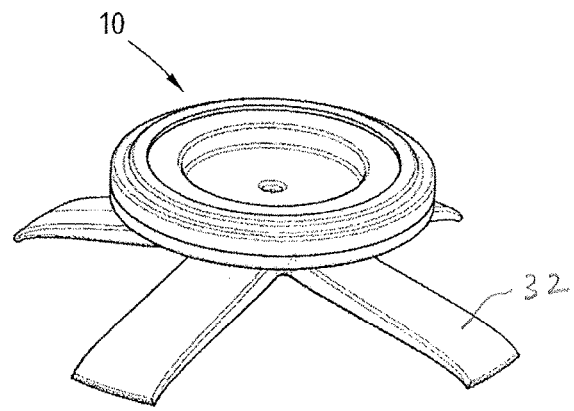
Figure 3C:
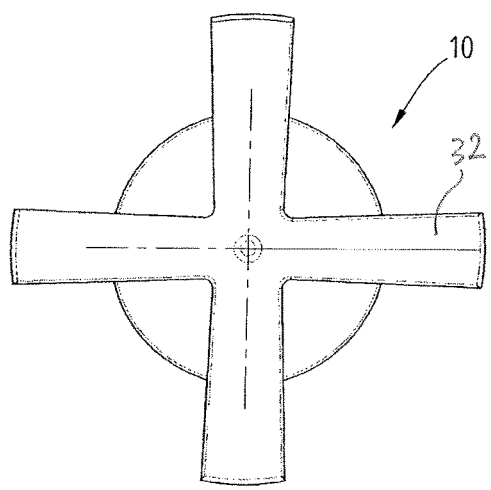

In this example, the closing element 10 comprises a sealing member 30 and a spring, which together form an integral whole and which are made of a polymer material, such as polyoxymethylene (POM) or a glass or carbon fiber reinforced polyolefin or PA. The sealing member 30 comprises a disc provided, along its circumference, with an elastomeric, e.g. rubber gasket 31. The spring comprises a plurality, e.g. four, leaf springs 32, which extend radially from the center of the disc and slightly downwards. The thickness of each of the leaf springs 32 gradually decreases towards its respective end (FIGS. 3B and 3D), whereas the width of each of the leaf springs 32 gradually increases in that same direction (FIGS. 3A and 3C). Also, the leaf springs 32 are slightly S-shaped in cross-section. The closing element 10 is clamped in between the ledge 23 and the seat 22 of the inner jacket 8.

In the closed position of the present closing valve 1, shown in FIG. 1, the sealing surface 21 of the inner jacket 8 abuts the annular gasket 15, thus closing off the space between the inner and outer casings from the surroundings, and the sealing member 30 is pressed by the spring onto the seat 22 about the central opening 9 in the inner jacket 8, thus closing off the inside of the inner container from the surroundings.

When a probe of a filling unit or a dispense head is pushed into the closing valve 1, the inner jacket 8 slides inwards with respect to the outer jacket 6 providing one or more vents 12 for de-aerating the space between the outer and inner casings during filling respectively letting in pressurized gas to expel fluid from the inner casing 50. Further, the closing element 10 is pressed inwards against the bias of the spring providing an opening for letting the fluid in respectively out.

The spring has a relatively high spring constant during initial depression, providing a good seal in the closed position, e.g. during storage and transport, and a relatively low spring constant along e.g. at least the second half of its stroke, adding relatively little strain and preventing the maximum strain level from exceeding a pre-determined threshold, e.g. 3%. As a result, the polymer material of the spring will suffer no or limited creep even if the container is exposed to high temperatures or remains connected to a dispense head for several hours or days and, when the container is disconnected, the closing element will properly close the inner casing 50 and the container can be stored until further use.

In the closing element 10 of the embodiment shown in FIGS. 1 to 4, the center of the disc comprises a concentric stepped recess, which serves to more evenly distribute stress and strain of over closing element 10 and to further suppress creep.

Figure 5:
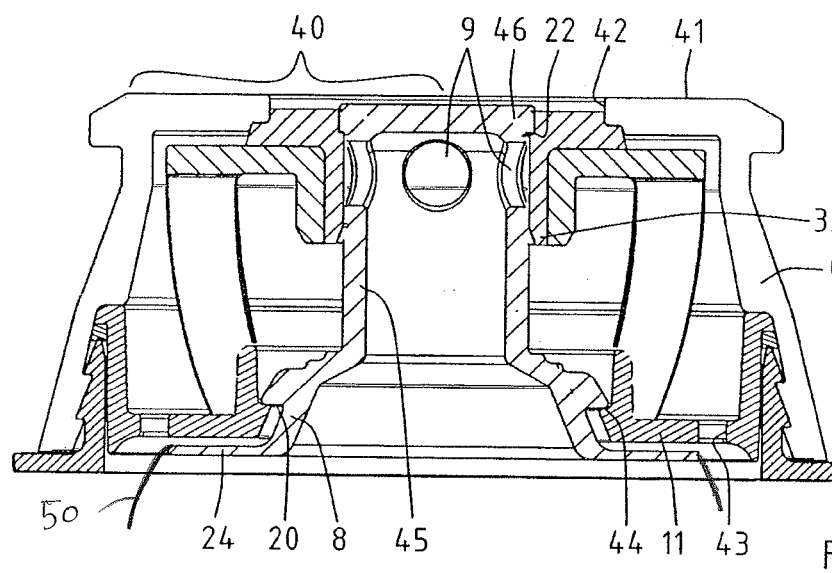
FIGS. 5 and 6 show cross-sections of a second embodiment of a closing valve according to an aspect of the present invention, in closed and opened conditions, respectively.
Figure 6:
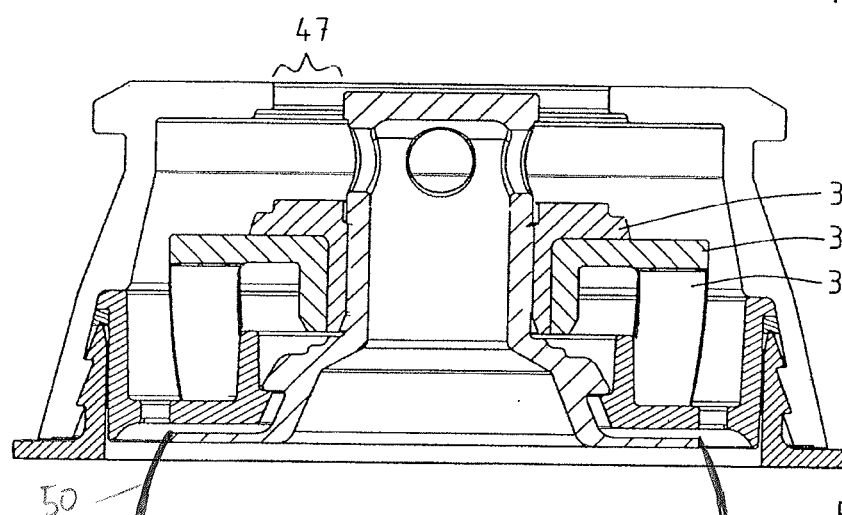

FIGS. 5 and 6 show cross-sections of a second embodiment of a closing valve 1 according to an aspect of the present invention, comprising an outer jacket 6 having a so-called German slider type keg fitting 40, also referred to as "flat fitting" or A type interface.

The outer jacket 6 comprises a flat upper surface 41 having a round opening 42 in its center and, in its bottom surface or on a separate element, e.g. an inner ring 11, a plurality of axially extending venting openings 43. The outer jacket 6, including the inner ring 11, is made of a polymer material, e.g. a glass or carbon fiber reinforced PP or PA. The outer jacket 6 or, in this example, the inner ring 11 comprises an annular ledge 44 facing upwards which cooperates with the inner jacket 8.

The inner jacket 8 comprises a cylindrical upper part 45 having a closed end 46, which is substantially flush with the upper surface 41 of the outer jacket 6, and, just below the closed end 46, one or more, e.g. four radially extending openings 9. The inner jacket 8 is made of a polymer material, e.g. a polyolefin, such as PP. The inner jacket 8 further comprises a seat 22 and, near its lower rim, an annular ledge 20 facing downwards and abutting the annular ledge 44 on the separate element 11. At its lower edge, the inner jacket 8 comprises a flange 24 to which an inner casing 50 for containing the fluid has been attached, e.g. by welding or gluing.

The annular opening 47 defined by the central opening 42 in the upper surface 41 of the outer jacket 6 and the closed end 46 of the inner jacket 8, is closed by a closing element 10.

Figures 7A, 7B:
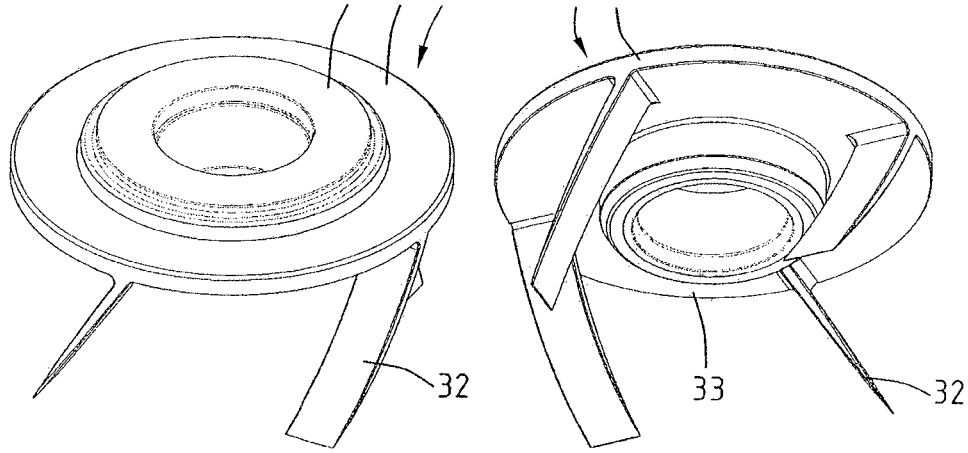
FIGS. 7A and 7B are perspective views of a closing element for use in the closing valve according to FIGS. 5 and 6.

In this example, the closing element 10, shown in detail in FIGS. 7A and 7B, comprises a sealing member 30 and a spring, which form an integral and which are made of a polymer material, such as POM or a glass or carbon fiber reinforced polyolefin or PA. The sealing member 30 comprises an annulus and, on the inner circumference of the annulus, a cylindrical skirt 33 and is provided with a similarly shaped elastomeric, e.g. rubber, gasket 31. The spring comprises a plurality, e.g. four, leaf springs 32, which extend tangentially and downwards from the sealing element 30. The thickness of each of the leaf springs 32 gradually decreases towards its respective end. The closing element 10 is clamped in between the outer jacket 6 and the seat 22 on the inner jacket 8 on the one hand and the upper surface of the inner ring 11 on the other.

In the closed position of the present closing valve 1, shown in FIG. 6, the annulus is pressed by the spring onto the seat 22 and onto the lower part of the opening 42, thus closing off the space between the inner and outer casings from the surroundings, and covering the radially extending openings 9 in the upper part 45 of the inner jacket 8 with the skirt 33, thus closing off the inside of the inner container from the surroundings.

When a probe of a filling unit or a dispense head for a German slider fitting, comprising an outer housing and a bell-shaped probe, is placed onto the upper surface 41 in a manner known in itself, the opening 47 is isolated from the surroundings by means of a gasket in the housing and the closing element 10 is pushed inwards against the bias of the spring by means of the bell-shaped probe, thus clearing the annular opening 47 and providing one or more vents 43 for de-aerating the space between the outer and inner casings during filling respectively letting in pressurized gas to expel fluid from the inner casing during dispensing. Subsequently, the skirt clears the radial openings 9 providing an opening for letting the fluid in respectively out.

The spring has a relatively high spring constant during initial depression, providing a good seal in the closed position, e.g. during storage and transport, and a relatively low spring constant along e.g. at least the second half of its stroke, adding relatively little strain and preventing the maximum strain level from exceeding a pre-determined threshold.

The invention is not restricted to the above-described embodiments which can be varied in a number of ways within the scope of the claims. For instance, when used in a Sankey type fitting, the closing element can comprise tangentially or axially extending projections and, when used in a German slider type fitting, the closing element can comprise at least partially radially extending projections.

The invention claimed is:

1. A closing valve for a container for a fluid, comprising:
   an outer jacket configured to be connected to an opening in the container or forming part of the container;
   an inner jacket accommodated inside the outer jacket and having an opening through which the fluid can be fed to or withdrawn from the container;
   a closing element positioned inside the inner jacket or between the inner jacket and the outer jacket and movable between at least a first position closing the opening of the container or the inner jacket opening and a second position clearing the opening of the container or the inner jacket opening; and
   wherein at least the closing element is made from a polymer material, and wherein the closing element comprises a sealing member and a spring, which urges the closing element into the first position, wherein the spring comprises a plurality of leaf springs extending from a peripheral section of the sealing member, having a middle portion that is curved, and having free outer ends abutting an annular stop of the outer or inner jacket, wherein the outer jacket comprises vents providing air channels between the inner and outer jackets leading to the opening of the container when the closing element is in the second position, and wherein a spring constant of the spring is relatively high during an initial portion of a depression and is relatively low during at least a second half of the depression.

2. The closing valve according to claim 1, wherein, in the first position of the closing element, a maximum strain level in the spring is less than 1%.

3. The closing valve according to claim 1 wherein, in the second position of the closing element, a maximum strain level in the spring is less than a proportional limit of strain.

4. The closing valve according to claim 1 and further comprising an inner ring disposed in the outer jacket, wherein the closing element releasably engages the inner jacket, and wherein the inner jacket engages the inner ring.

5. The closing valve according to claim 1, wherein the parts of the inner and outer jackets that, upon connecting a filling unit or a dispense head to the closing valve, contact that filling unit or dispense head are shaped complementary to a European or American Sankey type keg fitting, a German slider type keg fitting or a Grundy type fitting.

6. The closing valve according to claim 1, wherein the outer and inner jackets are made of a polymer material.

7. The closing valve according to claim 1, wherein the sealing member comprises a solid disc having a perimeter edge, and wherein the perimeter edge engages the inner jacket opening in the first position.

8. The closing valve according to claim 1, wherein the closing valve is configured for use in a positive pressure dispense system and the sealing member has a concentric stepped recess.

9. A container for fluids comprising: an outer casing made of a material, which is rigid such that it is resistant to a working pressure, a gas and liquid tight inner casing of a flexible material located inside the outer casing, wherein the material of the inner casing is collapsible under action of the working pressure, and a closing valve comprising: an outer jacket configured to be connected to an opening in the container or forming part of the container, an inner jacket accommodated inside the outer jacket and having an opening through which the fluid can be fed to or withdrawn from the container, and a closing element positioned inside the inner jacket or between the inner jacket and the outer jacket and movable between at least a first position closing the opening of the container or the inner jacket opening and a second position clearing the opening of the container or the inner jacket opening, wherein at least the closing element is made from a polymer material, and wherein the closing element comprises a sealing member and a spring, which urges the closing element into the first position, wherein the spring comprises one or more resilient projections, and wherein a thickness of the one or more resilient projections gradually decreases in a direction away from the sealing member, wherein the outer jacket comprises vents connecting a space between the outer and inner casings to the opening of the container via the outer jacket when the closing element is in the second position.

10. The container according to claim 9, wherein a spring constant of the spring is relatively high during an initial portion of a depression and is relatively low during at least the a second half of the depression.

11. The container according to claim 9, wherein, in the first position of the closing element, a maximum strain level in the spring is less than 1%.

12. The container according to claim 9, wherein, in the second position of the closing element, a maximum strain level in the spring is less than a proportional limit of strain.

13. The container according to claim 9 and further comprising an inner ring disposed in the outer jacket, wherein the closing element releasably engages the inner jacket, and wherein the inner jacket engages the inner ring.

14. The container according to claim 9, wherein the parts of the inner and outer jackets that, upon connecting a filling unit or a dispense head to the closing valve, contact that filling unit or dispense head are shaped complementary to a European or American Sankey type keg fitting, a German slider type keg fitting or a Grundy type fitting.

15. The container according to claim 9, wherein the outer and inner jackets are made of a polymer material.

16. The container according to claim 9, wherein the closing element comprises a disc having a concentric stepped recess.

17. The container according to claim 9, wherein the closing valve is configured for use in a positive pressure dispense system.

* * * * *